United States Patent
Tegen et al.

(10) Patent No.: US 10,413,845 B1
(45) Date of Patent: *Sep. 17, 2019

(54) PROCESSES FOR SOLVENT EXTRACTION OF CANNABINOIDS, TERPENES AND FLAVONOIDS FROM BIOMASS

(71) Applicant: SOCATI TECHNOLOGIES, Tumwater, WA (US)

(72) Inventors: Mark G. Tegen, Seattle, WA (US); Joon Cho, Tumwater, WA (US); William Rusty Sutterlin, Tuscaloosa, AL (US)

(73) Assignee: SOCATI TECHNOLOGIES, Tumwater, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/259,616

(22) Filed: Jan. 28, 2019

Related U.S. Application Data

(60) Provisional application No. 62/779,862, filed on Dec. 14, 2018, provisional application No. 62/781,958, filed on Dec. 19, 2018.

(51) Int. Cl.
| | |
|---|---|
| *A61K 36/00* | (2006.01) |
| *B01D 11/04* | (2006.01) |
| *A61K 36/185* | (2006.01) |

(52) U.S. Cl.
CPC ........ *B01D 11/0492* (2013.01); *A61K 36/185* (2013.01); *A61K 2236/15* (2013.01); *A61K 2236/33* (2013.01); *A61K 2236/39* (2013.01); *A61K 2236/53* (2013.01)

(58) Field of Classification Search
CPC ........................................................ A61K 36/00
USPC ........................................................... 424/725
See application file for complete search history.

(56) References Cited

U.S. PATENT DOCUMENTS

| | | |
|---|---|---|
| 6,403,126 B1 | 6/2002 | Webster et al. |
| 7,344,736 B2 | 3/2008 | Whittle et al. |
| 9,044,390 B1 | 6/2015 | Speier |
| 9,340,475 B2 * | 5/2016 | Mona, III ................. C11B 3/00 |
| 9,855,562 B2 | 1/2018 | Bates |
| 10,189,762 B1 | 1/2019 | Oroskar et al. |
| 2017/0008870 A1 | 1/2017 | Dibble et al. |
| 2018/0147247 A1 | 5/2018 | Ivanov |
| 2019/0010107 A1 | 1/2019 | Oroskar et al. |

FOREIGN PATENT DOCUMENTS

| | | |
|---|---|---|
| CA | 3000255 A1 | 9/2018 |
| EP | 1385595 B1 | 2/2012 |
| WO | 2017194173 A1 | 11/2017 |
| WO | 2019010419 A1 | 1/2019 |

OTHER PUBLICATIONS

Mousas et al., "Pulmonary Radiation Injury" Chest, 1997, v 111, p. 1061-1076.

\* cited by examiner

*Primary Examiner* — Michael V Meller
(74) *Attorney, Agent, or Firm* — Greer, Burns & Crain, LTD.; Gregory P. Einhorn

(57) ABSTRACT

In alternative embodiments, provided are industrial processes and methods for extracting or removing cannabinoids, flavonoids and terpenes from plant materials such as trichomes. In alternative embodiments, the cannabinoids, flavonoids and terpenes are extracted or removed from the plant materials using a non-polar, organic solvent, or a mixture of non-polar, organic solvent and polar, organic solvent.

1 Claim, 1 Drawing Sheet

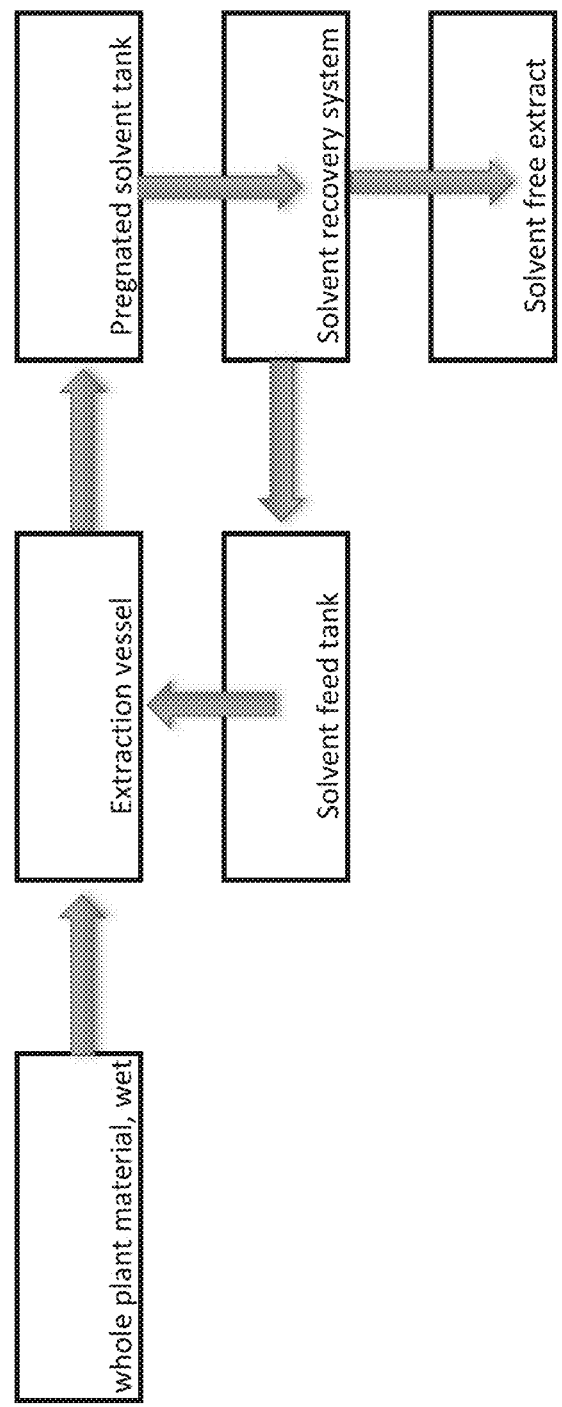

PROCESSES FOR SOLVENT EXTRACTION OF CANNABINOIDS, TERPENES AND FLAVONOIDS FROM BIOMASS

This application is a Track I Prioritized Examination Nonprovisional application under 35 USC 111(a) claiming benefit of priority to U.S. Provisional Application Ser. No. 62/779,862, filed Dec. 14, 2018, and U.S. Provisional Application Ser. No. 62/781,958, filed Dec. 19, 2018. The aforementioned applications are expressly incorporated herein by reference in their entirety and for all purposes.

FIELD OF THE INVENTION

This invention generally relates to chemical engineering and organic chemistry. In alternative embodiments, provided are industrial processes and methods for extracting or removing cannabinoids, flavonoids and terpenes from plant materials such as trichomes. In alternative embodiments, the cannabinoids, flavonoids and terpenes are extracted or removed from the plant materials using: a non-polar, organic solvent; a polar, organic solvent; or, a mixture of non-polar, organic solvent and polar, organic solvent.

BACKGROUND OF THE INVENTION

The production of trichomes can be observed in many species of plants throughout nature, taking on various physical forms as well as serving many different purposes. For example, trichomes found on some carnivorous plants aid in helping to catch prey. In *cannabis*, trichomes function as a defense mechanism. When female *cannabis* plants begin to produce flowers in the wild, they often become vulnerable to various insects and animals as well as non-living environmental variables such as potentially harmful UV rays. Trichomes serve as a deterrent for animals because their bitter taste and strong aromas render *cannabis* flowers unpalatable. At the same time, they also serve a dual function in protecting their plants from damaging winds and even some varieties of fungal growth. Bulbous trichomes are the smallest of the bunch, and they appear on the surface of the entire plant. Bulbous trichomes are as small as 10-15 micrometers, which is tiny enough to only be comprised of a handful of cells. Capitate sessile trichomes are slightly larger and contain both a head and a stalk. Capitate-stalked trichomes range from anywhere between 50-100 micrometers wide, meaning they're much larger and can actually be seen by the naked eye. Their structure consists of a stalk comprised of epidermal and hypodermic cells that build up to a basal cell which attaches to a large gland head. This gland head, held together by a waxy cuticle layer, serves as the epicenter for cannabinoid and terpenoid synthesis.

The importance of the process of extraction has increased with the growing global awareness of the medicinal, wellness and nutritional benefits of *Cannabis* plant extracts. In the example of hemp species of *Cannabis* it has been discovered that compounds present on the plant provide medicinal benefit for such conditions as inflammation, pain, nausea and epilepsy. There are some 60 bio-active compounds within the *Cannabis* plant. Some of these compounds are predicted to be valuable natural-source drugs which may not be associated with the side effects which plague commercial synthetic drugs.

Various methods of solvent extraction have been developed to separate the cannabinoids and terpenes from the non-cannabinoid and terpene biomaterial. Concentration of the cannabinoids and terpenes by solvent extraction is widely practiced and allows for the development of a wide variety of consumer products such as cannabinoid containing baked goods, gummies, sprays, drinks and other forms of cannabinoid products.

Industry has evolved three primary methods of solvent extraction including but not limited too super critical carbon dioxide, cold ethanol extraction and compressed butane extraction. Typical industrial practice is to first dry the fresh harvested whole plant material to about 5% to 10% moisture from a starting moisture greater than 50%. Then the biomass is processed, usually by hand or a semi-automated process where each plant is individually fed into a machine by hand, to separate the plant stem and fan leaves from the flower and cannabinoid rich leaves. The flower and leaf material is then typically subjected to one of the 3 common extraction methods to obtain the cannabinoids and remaining terpenes from the dried plant.

For example, in Method for Continuous Extraction and Separation of Useful Compounds from Plant or Animal Material Patent Literature U.S. Pat. No. 6,403,126, Webster et al teaches a method of extracting cannabinoids, cannflavins or essential oils in which the solvent may be a petroleum-derived hydrocarbon (for example: toluene or trimethylpentane); a low molecular weight alcohol (for example ethanol); a low molecular weight chlorinated hydrocarbon (for example, choroform); dichloromethane; or, supercritical fluid such as $CO_2$; and various products from hemp lacking $A^9$-THC obtained by passing the extract over a chromatographic column. U.S. Pat. No. 9,782,691, Chess et al teaches a process in which super- or sub-critical $CO_2$ is, alone or with a lower vapor pressure gas or gases, collected and re-used in a closed-loop extraction process. U.S. Pat. No. 9,399,180, Ellis et al teaches a vertical extraction process in which liquid gas is applied at the top, a vacuum draws down the extractant, and the gas is removed by cooling and recycled. U.S. Pat. No. 8,048,304, Walbel et al teaches a process for increased efficiency in the recovery and recycle of gases used in an extraction process. U.S. Pat. No. 9,358,259, Hospodor et al teaches a process of extracting cannabinoids in which the solvent is passed through the material many times in a cycle, the extractant remaining behind in a collector tank from which the solvent is removed and recycled. U.S. Pat. Nos. 9,669,328, 9,789,147, and 9,844,740, Jones, teach a process of extraction in which extraction takes place using liquid gases after which the product is used as is. The methods described lack the ability to extract cannabinoids and terpenes from the surface trichomes of whole wet plant material.

Hemp-derived cannabinoid use is rapidly expanding and more effort must be made to improve the extraction efficiency and overall extraction process economics. The current method of hand harvesting the hemp followed by drying and physical processing of the plant to remove stem and fan leaves is very costly, labor intensive and impractical when considering hand harvesting and drying thousands of acres and millions of pounds of biomass. Current extraction processes and methodology must be adapted for efficiency to modern outdoor farming and crop harvest methods. The ability to harvest the hemp biomass mechanically and process the plant in its intact and wet form will dramatically reduce the costs for growers, processors and consumers. Clearly a method of extracting cannabinoids and terpenes from whole plant wet biomass is needed.

SUMMARY OF THE INVENTION

In alternative embodiments, provided are industrial processes or methods for extracting or isolating a cannabinoid, a terpene or a flavonoid (or bioflavonoid), from a trichome or a trichome fraction of pubescent plant, algae or lichen, the method comprising:

(a) washing, contacting or exposing the trichome or trichome fraction, or the pubescent plant, algae or lichen, with: at least one non-polar, organic solvent; at least one polar, organic solvent; or, a mix of at least one non-polar, organic solvent with (and) at least one polar, organic solvent, and collecting or separating the solvent from the trichome or trichome fraction, or the pubescent plant, algae or lichen; or (b) (i) providing a pubescent plant or plant part, an algae or an algae part, or a lichen or lichen part comprising a trichome or a trichome fraction, (ii) providing: at least one non-polar, organic solvent; at least one polar, organic solvent; or, a mix of at least one non-polar, organic solvent with (and) at least one polar, organic solvent, (ii) washing, contacting or exposing the trichome or trichome fraction, or the pubescent plant, algae or lichen, with the at least one solvent or solvent mix, wherein optionally the washing, contacting or exposing is done in a reaction vessel and (iii) collecting or substantially removing the at least one solvent or solvent mix, thereby extracting or isolating (or substantially isolating) the cannabinoid, terpene or flavonoid (or bioflavonoid) from the trichome or trichome fraction of the pubescent plant, algae or lichen.

In alternative embodiments, of methods as provided herein:

the pubescent plant or plant part is a hemp or a marijuana plant or a plant of the family Cannabaceae;

the pubescent plant or plant part, the algae or algae part, or the lichen or lichen part, other than harvesting or collecting, is unprocessed or has not been physically processed, or has not been exposed to: a solvent or aqueous solution; a heating or drying process; a dehydration process; a crushing process; and/or, a chopping, macerating or mincing process, since (after) its harvest;

the pubescent plant or plant part, the algae or algae part, or the lichen or lichen part, other than harvesting or collecting, is subjected to: a heating or drying process; a dehydration process; a crushing process; and/or, a chopping, macerating or mincing process, since (after) its harvest;

the plant of the family Cannabaceae is a plant of the genus *Cannabis*, *Humulus* or *Celtis*, and optionally the plant of the genus *Cannabis* is a *Cannabis sativa*, *Cannabis indica* or a *Cannabis ruderalis;* the trichome is a glandular trichome;

the trichome or trichome fraction is isolated, or is substantially isolated, from the pubescent plant, algae or lichen before the washing, contacting or exposing of the trichome or trichome fraction with the at least one solvent (e.g., polar, organic solvent; non-polar, organic solvent, or mixture thereof); and/or the trichome or trichome fraction is not isolated from the pubescent plant, algae or lichen before the washing, contacting or exposing of the trichome or trichome fraction with the at least one solvent (e.g., polar, organic solvent; non-polar, organic solvent, or mixture thereof).

In alternative embodiments, methods as provided herein comprise continuously extracting and separating the cannabinoid, terpene and/or flavonoid compounds from the trichome or trichome fraction, or from the pubescent plant, algae or lichen, by a method comprising:

(a) feeding the trichome or trichome fraction, or the pubescent plant, algae or lichen, into a vessel;

(b) feeding the liquid non-polar, organic solvent; polar, organic solvent; or mixture thereof into the vessel to: saturate (or substantially saturate) the trichome or trichome fraction, or the pubescent plant, algae or lichen, in the vessel with the liquid non-polar, organic solvent polar, organic solvent; or mixture thereof; or, to create a mixture of (i) liquid non-polar, organic solvent polar, organic solvent; or mixture thereof, and (ii) trichome or trichome fraction, or pubescent plant, algae or lichen, thereby dissolving the cannabinoids, terpenes and or flavonoids in (or into) the trichome or trichome fraction, or the pubescent plant, algae or lichen, into the liquid non-polar, organic solvent; polar, organic solvent; or mixture thereof, wherein optionally the vessel is heated before or during the feeding and saturating process, and optionally the vessel is heated to between about 37° C. and 100° C., and optionally the mixture is agitated during all or part of the saturating process, and optionally the liquid non-polar, organic solvent; polar, organic solvent; or mixture thereof, is removed, or substantially removed, from the vessel, and optionally only the liquid non-polar, organic solvent; polar, organic solvent; or mixture thereof, is removed, or substantially removed, from the vessel, or substantially most of the trichome or trichome fraction, or the pubescent plant, algae or lichen, remains in the vessel after removal of the liquid non-polar, organic solvent; polar, organic solvent; or mixture thereof.

In alternative embodiments, in the methods as provided herein the at least one non-polar, organic solvent comprises: an aliphatic hydrocarbon, a 1,4 dioxane, a chloroform, a dichloromethane, a diethyl ether, a terpene, a hemiterpene, a monoterpene, a diterpene, a limonene, a humulene, a pinene, a myrcene, a caryophylene, acetone, benzene or a substituted benzene, toluene, a xylene, ethyl acetate, propyl acetate, butyl acetate, tetrahydrofuran, tetrahydropyran, or any mixture thereof.

In alternative embodiments, in the methods as provided herein the aliphatic hydrocarbon comprises a pentane, a cyclopentane, a hexane, a cyclohexane, a heptane, diethyl ether, dipropyl ether, dibutyl ether or any mixture thereof.

In alternative embodiments, in the methods as provided herein the at least one non-polar, organic solvent further comprises a polar, organic solvent, to make a mixture of the polar, organic solvent and non-polar, organic solvent. In alternative embodiments, methods as provided herein use only at least one polar, organic solvent (as a solvent).

In alternative embodiments, the at least one polar, organic solvent can comprise at least one organic alcohol, and optionally the at least one organic alcohol comprises methanol, ethanol, propanol, isopropanol, butanol, pentanol, hexanol, heptanol or octanol or a mixture thereof. In alternative embodiments, the mixture of the polar, organic solvent and non-polar, organic solvent can have more polar, organic solvent than non-polar, organic solvent, or the mixture of the polar, organic solvent and non-polar, organic solvent has about 1% to 100% more polar, organic solvent than non-polar, organic solvent.

In alternative embodiments, the mixture of the polar, organic solvent and non-polar, organic solvent can comprise: a chloroform:methanol mixture, optionally a 65:35 chloroform:methanol mixture; a chloroform:ethanol mixture, optionally a 65:35 chloroform:ethanol mixture; a chloroform:propanol, optionally a 65:35 chloroform:propanolol mixture; or, a chloroform:isopropanol mixture, optionally a 65:35 chloroform:isopropanol mixture.

In alternative embodiments, the washing, contacting or exposing the trichome or trichome fraction, or the pubescent plant, algae or lichen, with the at least one non-polar or organic solvent lasts for a period of between about 1 minute to about 48 hours, or for a period of time of between about 1 minute to 60 minutes, between about 1 minute to 120 minutes, or between about 1 minute to 480 minutes. In alternative embodiments, the washing, contacting or exposing the trichome or trichome fraction, or the pubescent plant, algae or lichen, with the at least one non-polar or organic solvent comprises immersion, spraying, washing, counter current liquid solid contacting or any combination thereof. In alternative embodiments, the trichome or trichome fraction, or the pubescent plant, algae or lichen, after the washing, contacting or exposing to the at least one non-polar, organic solvent, is processed for harvesting or extracting residual solvent removal, and optionally techniques or methods for harvesting or extracting residual solvent removal comprise spray drying, air stripping, gas stripping, vacuum stripping, heating, evaporation, washing or any combination thereof.

In alternative embodiments, the methods as provided herein further comprise removing residual solvent (e.g., at least one non-polar, organic solvent; at least one polar, organic solvent, or mixture thereof), wherein optionally techniques or methods for removing the residual one non-polar or organic solvent comprise spray drying, air stripping, gas stripping, vacuum stripping, heating, evaporation, washing or any combination thereof.

In alternative embodiments of the methods as provided herein, the trichome or trichome fraction, or the pubescent plant, algae or lichen, is fed through a conveyor into an extraction unit and optionally is sprayed (optionally continuously sprayed) with the at least one non-polar or organic solvent.

The details of one or more exemplary embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

DESCRIPTION OF DRAWINGS

FIG. 1 illustrates an exemplary process as provided herein to extract and separate products *cannabis* species.

Like reference symbols in the various drawings indicate like elements.

DESCRIPTION OF THE INVENTION

In alternative embodiments, provided are industrial processes and methods for extracting or removing cannabinoids and terpenes from plant trichomes. In alternative embodiments, the cannabinoids and terpenes are extracted or removed from the plant trichomes using a non-polar or an organic solvent.

A key aspect of the industrial processes and methods as provided herein is understanding the nature and location of the target cannabinoids and terpenes when extracting from a plant trichome, e.g., from a hemp or a *Cannabis*. The cannabinoids, and many terpenes, are primarily located in the trichomes, which exist on the surface of the plant, primarily on the flower. The actual definition of trichome is "fine outgrowths or appendages on plants, algae, lichens, and certain protists." Originating from the Greek word "Trichōma," meaning "growth of hair," these tiny microscopic mushroom-looking protuberances are the very factories that produce the hundreds of known cannabinoids, terpenes, and flavonoids.

Cannabinoid synthesis within the trichome begins as *cannabis* plants move into their bloom phase. As they begin to produce flowers, trichomes form along the outer surface of the above-ground plant vegetation and begin to transport vacuoles and plastids from their stalk into the gland head. At this point, cells within the gland head will begin to metabolize and form precursors for what will eventually become cannabinoids. The rate and concentration at which a *cannabis* plant produces trichomes will be contingent on both genetics well as some environmental factors. Though plants containing higher concentrations of trichomes don't always produce the highest concentration of cannabinoids and/or terpenes, variables such as UV light greatly affect cannabinoid and terpene synthesis within the trichome head.

Whether alive on a vine or harvested, trichomes are incredibly volatile and risk destruction and/or degradation at the hands of many catalysts, including but not limited to: physical contact or agitation, heat, light, oxygen and time. Not only do the trichomes themselves risk damage when exposed to these elements, but the essential oils within them risk degradation. There are ways to dramatically slow degradation of trichomes by carefully handling *cannabis* flowers both during propagation and post harvest. By limiting physical contact and agitation to the flowers themselves, trichomes may be preserved on the plant for longer periods of time. Those looking to extend the shelf life of trichomes beyond that of the plants they came from often resort to extraction techniques. An extraction in this context may be defined as the process of either mechanically or chemically removing trichomes from the plant itself.

With the location of the cannabinoids and terpenes determined we now need to understand the nature of the cannabinoids and terpenes present in the trichomes. Cannabinoids and cannabinoid acid species can be broadly understood as being non-polar. Terpenes and flavonoids present in the trichome as well can be broadly understood as non-polar. An aspect of the current industrial practice of hand separating the flowers from the stems causes physical damage to the trichomes and likely trichome losses. In addition, the drying process causes additional losses of volatile terpenes to the atmosphere. Therefore, methods as provided herein for extracting cannabinoids, terpenes and flavonoids from a whole wet plant will minimize the physical handling losses, and eliminating the drying process will help preserve valuable terpenes and eliminate the energy required for drying of the plant material.

In alternative embodiments, an organic non-polar solvent is used to wash and dissolve cannabinoids and terpenes from e.g., a whole wet plant, trichome or trichome fraction, or the pubescent plant, algae or lichen. The use of an organic non-polar solvent to wash and dissolve the cannabinoids and terpenes present in the trichomes can be a straightforward protocol when water is present. The organic non-polar solvent saturated with cannabinoids and terpenes will phase separate from any water that may or may not be present in the extract solution after contacting.

In alternative embodiments, a polar organic solvent, e.g., a polar organic solvent immiscible in water is used to wash and dissolve cannabinoids and terpenes from e.g., a whole wet plant, trichome or trichome fraction, or the pubescent plant, algae or lichen. In some embodiments, use of polar, organic solvents that is immiscible in water such as pentanol, hexanol or octanol also can be a straightforward protocol when water is present—the polar, organic solvents immiscible in water (e.g., pentanol, hexanol or octanol) phase separates from water.

In alternative embodiments, provided herein are batch, semi-continuous batch or continuous processes which offer significant improvements and advantages over current techniques used. In alternative embodiments, whole plants are mechanically harvested using e.g., a combine and sickle bar or a similar whole plant cutting device, and then taken for extraction, thereby eliminating the manual labor associated with hand harvesting and the energy needed for drying.

In alternative embodiments, non-polar solvent used in processes and methods as provided herein comprise: aliphatic hydrocarbons, pentane, cyclopentane, hexane, cyclohexane, heptane, cyclohentane, a pentene, a cylcopentene, a hexene, a cylohexene, acetone, a benzene or a substituted benzene, toluene, a xylene (e.g., o-xylenes, m-xylene, p-xylene), methyl acetate, ethyl acetate, propyl acetate, butyl acetate, tetrahydrofuran, tetrahydropyran, diethyl ether, dipropyl ether, dibutyl ether, 1,4-dioxane, chloroform, dichloromethane, dichloroethane, freon, a terpene, a hemiterpene, a monoterpene, a diterpene, limonene, humulene, pinene, myrcene, or caryophylene or any combination or mixture thereof.

In alternative embodiments, the trichome or trichome fraction, or the pubescent plant, algae or lichen, biomass used in extraction can comprise wet material, dried material, stock stems and leaves can be removed or present. Wet material can be present in combination with dried material at any ratio. The biomass can be sized reduced or a whole plant.

In alternative embodiments, the trichome or trichome fraction, or the pubescent plant, algae or lichen, biomass (e.g., the hemp or *Cannabis* biomass) is processed with the at least one solvent, e.g., non-polar, organic solvent; polar, organic solvent, or mixture thereof. Techniques for processing comprise immersion, spraying, washing, intermittent immersion, continuous counter current or co-current liquid solid contacting. Solvent biomass contacting can range for a period of 1 minute to 48 hours.

In one embodiment, hemp or *Cannabis* is used as the material to process. There are different ways to prepare the hemp or *Cannabis* for extraction. Typically flower of the female plant contain the highest quantities of cannabinoids. The preparation can comprise whole intact wet plant, whole intact dry plant material, chopped whole wet plant, chopped whole dry plant, wet flower and leaf, dry flower and leaf, or any combination thereof.

In alternative embodiments, the plant material comprises flowering plants in the family Cannabaceae. *Cannabis sativa, Cannabis indica, Cannabis ruderalis*, hemp or any combination thereof.

In alternative embodiments, the plant material is fed into a vessel using a surge bin, a metered hopper, or an auger or other device. If the device is to be used in a continuous fashion, the feed system will be configured to provide a constant volume of the prepared feedstock. In that regard, the feed method will require a reservoir of some type or in itself be a continuously fed device.

In alternative embodiments, the plant material, e.g., the pubescent plant, algae or lichen, is contacted with the at least one solvent, e.g., non-polar, organic solvent; polar, organic solvent, or mixture thereof. In alternative embodiments, the methods comprise immersion, spraying, washing, counter current liquid solid contacting or any combination thereof.

In alternative embodiments, the non-polar, organic solvent comprises at least one of: aliphatic hydrocarbons, pentane, cyclopentane, hexane, cyclohexane, heptane, acetone, benzene, toluene, xylenes, ethyl acetate, propyl acetate, butyl acetate, tetrahydrofuran, tetrahydropyran, diethyl ether, dipropyl ether, dibutyl ether, 1,4-dioxane, chloroform, dichloromethane, a terpene, a terpenoid, a hemiterpene, a monoterpene, a diterpene, limonene, humulene, pinene, myrcene, caryophylene, or any combination thereof.

In alternative embodiments, the cannabinoids and terpenes are dissolved from the surface of the plant material by the one or more solvents (e.g., at least one non-polar, organic solvent; polar, organic solvent; or, mixture thereof) contacting the surface of the plant material. The extracted biomass is then processed for residual solvent, e.g., residual solvent is removed or substantially removed. Techniques known to those skilled in the art (e.g., for the contacting of the solvent with the plant material) comprise spray drying, air stripping, gas stripping, vacuum stripping, heating, evaporation, washing or any combination thereof.

In alternative embodiments, the cannabinoid, flavonoid and/or terpene rich solvent solution is then processed to separate the solvent from the cannabinoids and/or terpenes, or, in the case of winterization or crystallization, to separate the cannabinoids and/or terpenes from the solvent. Techniques that can be used for this separation can include any known to those skilled in the art, including batch distillation, continuous distillation, vacuum distillation, gas stripping, mole sieve filtration, nano filtration, filtration, winterization or crystallization, or any combination thereof. In alternative embodiments, the processed or recovered solvent or solvent mixture is then recycled, stored for future use and/or disposed.

In alternative embodiments, a whole wet trichome or trichome fraction, or the pubescent plant, algae or lichen (collectively and individually referred to a "biomass"), e.g., hemp is fed through a conveyor into an extraction unit. The biomass, e.g., hemp, can be continuously sprayed with: the at least one non-polar, organic solvent, e.g., a terpene or terpene mixture or any combination thereof; or, a mixture of at least one polar, organic solvent and at least one non-polar and organic solvent; or, at least one polar, organic solvent, e.g., an organic alcohol.

In alternative embodiments, the biomass, e.g., hemp, is contacted with the solvent for a period of time from 1 minute to 60 minutes, 1 minute to 120 minutes, 1 minute to 480 minutes. In alternative embodiments, the solvent drains through the biomass and is collected. In alternative embodiments, the collected solvent or solvent mixture is reintroduced, e.g., as the biomass continuously travels on a conveyor through a solvent contacting system. In alternative embodiments, the biomass, e.g., hemp, is contacted with the solvent or solvent mixture at the temperature ranging from between about −10° C. to the boiling point of the solvent used, or from between about −10 to 100° C. for a period of time from between 1 second to 480 minutes, or between about 1 minute (min) and 1 hour (hr), or between about 5 min and 2 hours, with or without agitation during all or part of the process.

In alternative embodiments, the biomass is introduced to a mixing tank, with or without heating. In alternative embodiments, the biomass is introduced into the mixing tank at a temperature of between about −10 to 100° C., or between about −5 to 80° C., or the temperature of the biomass is in the mixing tank raised to or lowered to, or kept at, at a temperature of between about −10 to 100° C., or between about −5 to 80° C.

In alternative embodiments, the solvent or solvent mixture is introduced to the tank in sufficient quantity as to provide for complete or near complete immersion of the biomass. In alternative embodiments, the biomass and solvent or solvent mixture are then subjected to mixing; however, mixing is not necessary but can improve extract yield. In alternative embodiments, the biomass is then removed or filtered from the solvent or solvent mixture.

In alternative embodiments, the solvent or solvent mixture is then removed by evaporation and optionally the cannabinoids and/or terpenes are recovered. In alternative embodiments, the solvent or solvent mixture is then removed by a rotary evaporator or other evaporating equipment, optionally at the temperature below the boiling point of the solvent or solvent mixture under a pressure ranging from between about the atmosphere pressure down to about 0.001 torr.

Winterization or Crystallization

In alternative embodiments, the cannabinoids and/or terpenes are recovered from (or substantially recovered from), or isolated from the solvent or solvent mixture by a winterization or crystallization process.

In alternative embodiments, before winterization or crystallization (or solidification) the initial cannabinoids and/or terpenes solvent mixture is (further) diluted with an organic solvent, e.g., a hexane or a terpene. In alternative embodiments, before winterization or crystallization the solvent mixture is diluted by between about 1% to 80%, or by between about 5% to 50%.

In alternative embodiments, before winterization or crystallization (or solidification) the initial cannabinoids and/or terpenes solvent mixture is concentrated, e.g., a portion of the non-polar, organic solvent or polar, organic solvent is removed before the winterization or crystallization (or solidification), or cooling, process.

In alternative embodiments, between about 1% to 90% of the non-polar, organic solvent or polar, organic solvent is removed before the winterization or crystallization (or solidification), or cooling, process.

In alternative embodiments, the winterization or crystallization (or solidification), or cooling, process comprises cooling the mixture until crystals of cannabinoids, flavonoids and terpenes are formed, or until the cannabinoids, flavonoids and/or terpenes solidify. In alternative embodiments, the cooling process comprise further cooling after the crystallization (or solidification) begins. In alternative embodiments, the winterization or crystallization (or solidification), or cooling, process comprises cooling the mixture to a temperature of between about −10° C. to about −90° C., between about −20° C. to about −85° C., or between about −50° C. to about −80° C. In alternative embodiments, the winterization or crystallization (or solidification), or cooling, process comprises cooling for between about 10 to 30 minutes (min) to about 1, 2, 3, 4, 5 or 6 hours (hrs). In alternative embodiments, the winterization or crystallization (or solidification), or cooling, process lasts for between about 1 to 24 hrs. In alternative embodiments, the process comprises multiple cooling, crystal harvesting or isolation, and re-cooling cycles.

In alternative embodiments, the winterization or crystallization (or solidification), or cooling, process comprises a process as described in U.S. Pat App Pub no US2017/0008870A1; U.S. Pat. No. 3,755,389; or U.S. Pat. No. 2,705,723.

In alternative embodiments, the winterization or crystallization (or solidification), or cooling, process is done in a refrigerator, a freezer or using dry ice (or any system that lowers the temperature to about −109.3 degrees Fahrenheit (−78.5 degrees C.)) or liquid nitrogen. The winterization or crystallization (or solidification), or cooling, process can be done under vacuum or pressure.

In alternative embodiments, the solids or crystals of the cannabinoids, flavonoids and/or terpenes are separated from the liquid solvent by filtration. In alternative embodiments, the solids or crystals of the cannabinoids, flavonoids and/or terpenes are decanted away from the liquid solvent. In alternative embodiments, the solids or crystals of the cannabinoids, flavonoids and/or terpenes are sheet or ball crystals. In alternative embodiments, the solids or crystals of the cannabinoids, flavonoids and/or terpenes need to be scraped or physically removed from the container or reaction vessel from which they were cooled and subsequently crystallized or solidified.

In alternative embodiments, the cannabinoid, flavonoid and/or terpene solids or crystals are at least 70% pure, or are between about 75% to 99.9% or 100% pure (e.g., free of impurities, or non-cannabinoid, flavonoid and/or terpene substances or solvent), or are about (or at least about) 75%, 80%, 85%, 90%, 95%, 98%, 99%, 99.5%, 99.9% or 100% pure.

It is understood that those skilled in the art might find alternative embodiments to the methods described herein, which are meant to describe the principles involved in the extraction conditions, which include the collection of the extractants and solvent, the collection of the extractants or solutes (the compounds of interest being isolated), and/or the removal of the spent material, the subsequent separation of the extractant from the solvent, and the optional step or steps of isolating one or more of the products of the extraction, where these alternative embodiments fall within the scope of this methods as provided herein.

The invention will be further described with reference to the examples described herein; however, it is to be understood that the invention is not limited to such examples.

EXAMPLES

Example 1: Exemplary Methods 10 pounds of mature whole hemp plant was harvested. Between about 3 gram (g) to about 100 g samples of plant flower, leaf and stem was weighed for the experiments. The material was not dried or subjected to particle size reduction.

Three (3) samples of whole wet plant material was then prepared for extraction. Sample 257-A (control sample) was immersed in 1,500 ml of 65:35 mixture of chloroform:methanol overnight; sample 257-B was subjected to 5×60 second immersions in ambient hexane; sample 257-C was immersed in hexane for 15 minutes at ambient temperature; sample 257-D was immersed in hexane for 15 minutes at 40° C.; sample 257-E was immersed in hexane for 10 minutes at 60 C. 100 g of the weighed sample was immersed in dichloromethane (DCM) in a vessel at ambient temperature, and then the sample was taken out. This immersion was repeated 5 times. Another three 100 g samples were soaked in hexane in three different vessels with agitation under the conditions: at ambient temperature for 15 min; at 40° C. for 15 min; 60° C. for 15 min. A control sample was subjected to a 1,500 ml 65:35 mixture chloroform:methanol solution and let soak for 24 hours with agitation to represent 100% extraction of cannabinoids and used as a reference of total extractable cannabinoids.

| Exp No. | Extraction Method (100 g wet hemp in 1500 mL solvent) immersion in chloroform/methanol | Weight of dried extract (g) | Percentage of CBD in dried oil (%) | CBD weight in dried oil (g) | CBD weight extracted from 100 g wet hemp (g) | Percentage of CBD in 100 g wet hemp |
|---|---|---|---|---|---|---|
| 257-A | at ambient temperature overnight | 5.3119 | 34.7 | 1.84 | 1.84 | 1.84 |
| 257-B | 5 × 60 sec immersion in dichloromethane | 2.2821 | 62.6 | 1.43 | 1.43 | 1.43 |
| 257-C | immersion in ambient temperature hexane for 15 min | 2.7476 | 64.7 | 1.78 | 1.78 | 1.78 |
| 257-D | immersion in 40° C. hexane for 15 min | 3.3073 | 66.2 | 2.19 | 2.19 | 2.19 |
| 257-E | immersion in 60° C. hexane for 10 min | 2.2014 | 65.0 | 1.43 | 1.43 | 1.43 |

A number of embodiments of the invention have been described. Nevertheless, it can be understood that various modifications may be made without departing from the spirit and scope of the invention. Accordingly, other embodiments are within the scope of the following claims.

What is claimed is:

1. A method of isolating tetrahydrocannabinol, a terpene, or cannabidiol from hemp or *cannabis*, the method consisting essentially of:
   a) extracting hemp or *cannabis* with a solvent selected from the group consisting of propanol, isopropanol, butanol, pentanol, hexanol, heptanol, and octanol to produce an extract consisting essentially of an extracted hemp or *cannabis* consisting essentially of tetrahydrocannabinol, a terpene, or cannabidiol;
   b) evaporating the solvent portion of the extract to generate a substantially solvent-free extract consisting essentially of the tetrahydrocannabinol, terpene or cannabidiol;
   c) distilling the substantially solvent-free extract to isolate the tetrahydrocannabinol, the terpene or the CBD, and
   d) crystallizing the distilled, isolated tetrahydrocannabinol, terpene or cannabidiol to produce a crystallized, isolated tetrahydrocannabinol, terpene or cannabidiol.

* * * * *